(12) United States Patent
Macatangay

(10) Patent No.: US 9,925,031 B2
(45) Date of Patent: Mar. 27, 2018

(54) ENDOLUMINAL DEVICE WITH KINK-RESISTANT REGIONS

(75) Inventor: Edwin E. Macatangay, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 501 days.

(21) Appl. No.: 13/518,237

(22) PCT Filed: Dec. 8, 2010

(86) PCT No.: PCT/US2010/059495
§ 371 (c)(1),
(2), (4) Date: Jun. 21, 2012

(87) PCT Pub. No.: WO2011/081814
PCT Pub. Date: Jul. 7, 2011

(65) Prior Publication Data
US 2012/0265289 A1    Oct. 18, 2012

Related U.S. Application Data

(60) Provisional application No. 61/290,309, filed on Dec. 28, 2009.

(51) Int. Cl.
*A61F 2/82* (2013.01)
*A61F 2/07* (2013.01)
(Continued)

(52) U.S. Cl.
CPC ............ *A61F 2/07* (2013.01); *D03D 3/02* (2013.01); *D03D 13/008* (2013.01); *D03D 15/00* (2013.01);
(Continued)

(58) Field of Classification Search
CPC .... A61F 2/88; A61F 2/885; A61F 2/82; D03D 3/02; D03D 13/008; D03D 15/00; D10B 2331/04; D10B 2509/06
(Continued)

(56) References Cited

U.S. PATENT DOCUMENTS 4,561,439 A    12/1985    Bishop et al.
4,878,906 A    11/1989    Lindemann et al.
(Continued)

FOREIGN PATENT DOCUMENTS

WO    1991/012779    9/1991
WO    1996/021404    7/1996
(Continued)

OTHER PUBLICATIONS

International Search Report, PCT/US2010/059495, filed Dec. 8, 2010.
(Continued)

*Primary Examiner* — Shaun L David
(74) *Attorney, Agent, or Firm* — Brinks Gilson & Lione

(57) ABSTRACT

An endoluminal prosthesis having a tubular graft comprising a first biocompatible material having a first weave density comprising yarns aligned in a first direction interwoven with yarns aligned in a second direction, and a second biocompatible material having a second weave density less than the first weave density comprising yarns aligned in a first direction interwoven with yarns aligned in a second direction, the second biocompatible material spirally positioned throughout the entire length of the tubular graft around a central axis with respect to the first biocompatible material. An elongate member is attached along the length of the tubular graft. The tubular graft includes first regions comprising the first biocompatible material and second regions
(Continued)

containing the second biocompatible material. The elongate member is attached to the first regions of the tubular graft.

20 Claims, 7 Drawing Sheets

(51) Int. Cl.
| | | |
|---|---|---|
| *D03D 3/02* | (2006.01) | |
| *D03D 13/00* | (2006.01) | |
| *D03D 15/00* | (2006.01) | |
| *A61F 2/88* | (2006.01) | |
| *A61F 2/89* | (2013.01) | |

(52) U.S. Cl.
CPC . *A61F 2/88* (2013.01); *A61F 2/89* (2013.01); *A61F 2002/075* (2013.01); *A61F 2230/0067* (2013.01); *A61F 2250/0017* (2013.01); *A61F 2250/0029* (2013.01); *A61F 2250/0039* (2013.01); *D10B 2331/04* (2013.01); *D10B 2509/06* (2013.01)

(58) Field of Classification Search
USPC .................................. 623/1.13, 1.15, 1.32
See application file for complete search history.

(56) References Cited

U.S. PATENT DOCUMENTS

| | | |
|---|---|---|
| 4,886,062 A | 12/1989 | Wiktor |
| 5,226,913 A | 7/1993 | Pinchuk |
| 5,269,751 A | 12/1993 | Kaliman et al. |
| 5,282,824 A | 2/1994 | Gianturco |
| 5,314,472 A | 5/1994 | Fontaine |
| 5,316,023 A | 5/1994 | Palmaz et al. |
| 5,360,443 A | 11/1994 | Barone et al. |
| 5,370,653 A | 12/1994 | Cragg |
| 5,370,683 A | 12/1994 | Fontaine |
| 5,376,100 A | 12/1994 | Lefebvre |
| 5,443,498 A | 8/1995 | Fontaine |
| 5,476,506 A | 12/1995 | Lunn |
| 5,507,767 A | 4/1996 | Maeda et al. |
| 5,527,354 A | 6/1996 | Fontaine et al. |
| 5,554,182 A | 9/1996 | Dinh et al. |
| 5,591,195 A | 1/1997 | Taheri et al. |
| D390,957 S | 2/1998 | Fontaine |
| 5,747,128 A * | 5/1998 | Campbell et al. ........... 428/35.7 |
| 5,782,904 A | 7/1998 | White et al. |
| 5,800,456 A | 9/1998 | Maeda et al. |
| 5,843,166 A | 12/1998 | Lentz et al. |
| 5,865,723 A | 2/1999 | Love |
| 5,968,057 A | 10/1999 | Taheri |
| 5,984,965 A | 11/1999 | Knapp et al. |
| 6,019,779 A | 2/2000 | Thorud et al. |
| 6,042,605 A | 3/2000 | Martin et al. |
| 6,077,296 A | 6/2000 | Shokoohi et al. |
| 6,090,128 A | 7/2000 | Douglas |
| 6,137,060 A | 10/2000 | Avellanet |
| 6,156,062 A | 12/2000 | McGuiness |
| 6,156,063 A | 12/2000 | Douglas |
| 6,159,239 A | 12/2000 | Greenhalgh |
| 6,164,339 A * | 12/2000 | Greenhalgh ............ A61F 2/07 139/1 R |
| 6,187,036 B1 | 2/2001 | Shaolian et al. |
| 6,191,365 B1 | 2/2001 | Avellanet |
| 6,197,049 B1 | 3/2001 | Shaolian et al. |
| 6,210,422 B1 | 4/2001 | Douglas |
| 6,264,684 B1 | 6/2001 | Banas et al. |
| 6,261,316 B1 | 7/2001 | Shaolian et al. |
| 6,270,524 B1 | 8/2001 | Kim |
| 6,278,057 B1 | 8/2001 | Avellanet |
| 6,319,277 B1 | 11/2001 | Rudnick et al. |
| 6,331,188 B1 | 12/2001 | Lau et al. |
| 6,331,190 B1 | 12/2001 | Shokoohi et al. |
| 6,338,739 B1 | 1/2002 | Datta et al. |
| 6,361,637 B2 | 3/2002 | Martin et al. |
| 6,364,904 B1 | 4/2002 | Smith |
| 6,440,161 B1 | 8/2002 | Madrid et al. |
| 6,454,775 B1 | 9/2002 | Demarais et al. |
| 6,491,619 B1 | 12/2002 | Trauthen et al. |
| 6,500,202 B1 | 12/2002 | Shaolian et al. |
| 6,508,835 B1 | 1/2003 | Shaolian et al. |
| 6,517,570 B1 | 2/2003 | Lau et al. |
| 6,517,572 B2 | 2/2003 | Kugler et al. |
| 6,520,986 B2 | 2/2003 | Martin et al. |
| 6,530,935 B2 | 3/2003 | Wensel et al. |
| 6,551,350 B1 | 4/2003 | Thornton et al. |
| 6,565,596 B1 | 5/2003 | White et al. |
| 6,635,080 B1 | 10/2003 | Lauterjung et al. |
| 6,652,548 B2 | 11/2003 | Evans et al. |
| 6,660,030 B2 | 12/2003 | Shaolian et al. |
| 6,663,665 B2 | 12/2003 | Shaolian et al. |
| D484,979 S | 1/2004 | Fontaine |
| 6,673,103 B1 | 1/2004 | Golds et al. |
| 6,685,618 B2 | 2/2004 | Tam et al. |
| 6,685,696 B2 | 2/2004 | Fleischhacker et al. |
| 6,685,722 B1 | 2/2004 | Rosenbluth et al. |
| 6,685,736 B1 | 2/2004 | White et al. |
| 6,689,157 B2 | 2/2004 | Madrid et al. |
| 6,692,509 B2 | 2/2004 | Wensel et al. |
| 6,699,170 B1 | 3/2004 | Crocker et al. |
| 6,733,523 B2 | 5/2004 | Shaolian et al. |
| 6,770,087 B2 | 8/2004 | Layne et al. |
| 6,773,457 B2 | 8/2004 | Ivancev et al. |
| 6,866,680 B2 | 3/2005 | Yassour et al. |
| 6,923,828 B1 | 8/2005 | Wiktor |
| 6,926,725 B2 | 8/2005 | Cooke et al. |
| 6,929,709 B2 | 8/2005 | Smith |
| 6,951,572 B1 | 10/2005 | Douglas |
| 6,953,475 B2 | 10/2005 | Shaolian et al. |
| 6,974,471 B2 | 12/2005 | Van Schie et al. |
| 6,974,473 B2 | 12/2005 | Barclay et al. |
| 6,986,784 B1 | 1/2006 | Weiser et al. |
| 7,018,401 B1 | 3/2006 | Hyodoh et al. |
| 7,037,316 B2 | 5/2006 | McGuckin, Jr. et al. |
| 7,044,905 B2 | 5/2006 | Vidlund et al. |
| 7,060,092 B2 | 6/2006 | Kuribayashi et al. |
| 7,229,472 B2 | 6/2007 | DePalma et al. |
| 7,318,835 B2 | 1/2008 | Berra |
| 2001/0007954 A1 | 7/2001 | Shaolian et al. |
| 2002/0013617 A1 | 1/2002 | Matsutani et al. |
| 2002/0156523 A1 | 10/2002 | Lau et al. |
| 2002/0165603 A1 | 11/2002 | Thornton et al. |
| 2003/0088305 A1 | 5/2003 | Van Schie et al. |
| 2003/0130721 A1 | 7/2003 | Martin et al. |
| 2003/0149475 A1 | 8/2003 | Hyodoh et al. |
| 2004/0024443 A1 | 2/2004 | Dwyer et al. |
| 2004/0116960 A1 | 6/2004 | Demond et al. |
| 2004/0117003 A1 | 6/2004 | Ouriel et al. |
| 2005/0049574 A1 | 3/2005 | Petrick et al. |
| 2005/0075715 A1 | 4/2005 | Borges et al. |
| 2005/0085894 A1 | 4/2005 | Kershner |
| 2005/0137677 A1 | 6/2005 | Rush |
| 2005/0137680 A1 | 6/2005 | Ortiz et al. |
| 2005/0154448 A1 | 7/2005 | Cully et al. |
| 2005/0177246 A1 | 8/2005 | Datta et al. |
| 2005/0240261 A1 | 10/2005 | Rakos et al. |
| 2006/0004436 A1 | 1/2006 | Amarant et al. |
| 2006/0030926 A1 | 2/2006 | Berra |
| 2006/0142841 A1 | 6/2006 | Khosravi et al. |
| 2006/0265052 A1 | 11/2006 | You |
| 2007/0067024 A1 | 3/2007 | White et al. |
| 2007/0112412 A1 | 5/2007 | Shokoohi et al. |
| 2007/0198079 A1 | 8/2007 | Casey, II et al. |
| 2007/0207186 A1 | 9/2007 | Scanlon et al. |
| 2007/0208421 A1 | 9/2007 | Quigley |
| 2007/0215268 A1 | 9/2007 | Pingleton et al. |
| 2007/0299497 A1 | 12/2007 | Shaolian et al. |
| 2008/0082154 A1 | 4/2008 | Tseng et al. |
| 2008/0082158 A1 | 4/2008 | Tseng et al. |
| 2008/0082159 A1 | 4/2008 | Tseng et al. |
| 2008/0114445 A1 | 5/2008 | Melsheimer et al. |
| 2008/0147172 A1 | 6/2008 | White et al. |
| 2008/0195191 A1 | 8/2008 | Luo et al. |

(56) References Cited

U.S. PATENT DOCUMENTS

2008/0228262 A1 9/2008 Goldmann et al.
2008/0262594 A1 10/2008 Morris
2009/0030499 A1 1/2009 Bebb et al.
2011/0009951 A1* 1/2011 Bogert .................... 623/1.22

FOREIGN PATENT DOCUMENTS

| WO | 1999/044536 | 9/1999 |
|----|-------------|---------|
| WO | 2000/028922 | 5/2000 |
| WO | 2001/001887 | 1/2001 |
| WO | 2003/057079 | 7/2003 |
| WO | 2003/099166 | 12/2003 |
| WO | 2004/082533 | 9/2004 |

OTHER PUBLICATIONS

International Preliminary Report on Patentability, PCT/US2010/059495, filed Dec. 8, 2010.
Communication for EP Application No. 10793109.9, published as EP2519189 dated Nov. 7, 2012, communication dated Jun. 11, 2013, 6 pages.

* cited by examiner

ENDOLUMINAL DEVICE WITH KINK-RESISTANT REGIONS

This application is a National Stage application of International Application No. PCT/US2010/059495 filed Dec. 8, 2010, which claims the benefit of U.S. Provisional Application No. 61/290,309, filed Dec. 28, 2009, the entire contents of which are hereby incorporated herein by reference.

TECHNICAL FIELD

This invention relates generally to medical devices and particularly to medical devices that are implantable within the human or animal body for the repair of damaged vessels, ducts or other physiological passageways and cavities.

BACKGROUND OF THE INVENTION

The physiological passageways and cavities of human and animal bodies, for example, blood vessels and ducts, occasionally weaken or even rupture. One common surgical intervention for weakened, aneurismal or ruptured passageways or ducts involves the use of an endoluminal prosthesis to provide some or all of the functionality of the original, healthy passageway or duct and/or preserve any remaining vascular integrity by replacing a length of the existing passageway or duct wall that spans the site of failure or defect. Endoluminal prostheses may be of a unitary construction or may be comprised of multiple prosthetic modules.

SUMMARY OF THE INVENTION

The present invention seeks to provide an improved medical prosthesis. The term prosthesis is used herein to include implantable medical devices whether for replacement of a part of a vessel, for lining a vessel and for permanent or temporary use. The term endoluminal prosthesis is used herein to relate to a prosthesis which is able to be deployed in the lumen of a patient.

According to an aspect of the present invention, there is provided an endoluminal prosthesis as specified in claim 1.

Endoluminal prostheses of medical devices are described which may allow for increased flexibility while maintaining the integrity of an inner lumen thereof in tortuous anatomy.

In one embodiment, an endoluminal prosthesis may be a tubular graft having a first biocompatible material with a first weave density comprising yarns aligned in a first direction interwoven with yarns aligned in a second direction, and a second biocompatible material having a second weave density less than the first weave density comprising yarns aligned in a first direction interwoven with yarns aligned in a second direction. The second biocompatible material may be spirally positioned around a central axis with respect to the first biocompatible material throughout the entire length of the tubular graft. The tubular graft includes first regions comprising the first biocompatible material and second regions containing the second biocompatible material.

An elongate member may be attached at regions along the length of the tubular graft. The elongate member may be attached to the first regions of the tubular graft. In some embodiments, the second regions are narrower than the first regions. In other embodiments, the first biocompatible material comprises yarns having a first denier, and the second biocompatible material comprises yarns having a second denier smaller than the first denier.

In another embodiment, an endoluminal prosthesis may include a tubular graft comprising a first biocompatible material having a first flexibility and a second biocompatible material having a second flexibility greater than the first flexibility, the second biocompatible material spirally positioned around a central axis with respect to the first biocompatible material throughout the entire length of the tubular graft. An elongate member is attached along the length of the graft. The tubular graft includes first regions comprising the first biocompatible material and second regions containing the second biocompatible material. The elongate member is attached to the first regions of the tubular graft. In some embodiments, the first biocompatible material has a first weave density comprising yarns aligned in a first direction interwoven with yarns aligned in a second direction, and the second biocompatible material has a second weave density less than the first weave density comprising yarns aligned in a first direction interwoven with yarns aligned in a second direction. In other embodiments, the second regions are narrower than the first regions.

In yet another embodiment, an endoluminal prosthesis may include a tubular graft comprising a first biocompatible material having a first denier and a second biocompatible material having a second denier lower than the first denier and disposed on the graft in a helix. An elongate member having a plurality of turns is attached longitudinally and circumferentially attached to graft, the elongate member including a plurality of bends, each bend connecting a pair of first and second struts at a first angle, each of the first struts extending between adjacent bends in a first direction and each of the second struts extending between adjacent bends in a second direction, the second direction being different than the first direction. The tubular graft includes first regions comprising the first biocompatible material and second regions containing the second biocompatible material. The elongate member is attached to the first regions of the tubular graft.

The second regions in the endoluminal prosthesis provide specific areas for the endoluminal prosthesis to curve or fold when it is positioned in a tortuous, or curved, position. The second regions are less dense than the other regions of the endoluminal prosthesis, and are more susceptible to the effects of the force created when the endoluminal prosthesis is bent. When the endoluminal prosthesis is bent, the force applied to the endoluminal prosthesis is distributed in the precise areas defined by the thin regions. Thus, instead of the endoluminal prosthesis kinking in one particular area, the second regions of the endoluminal prosthesis allow for controlled folding in designated areas. This improvement is significant as it reduces possibility of kinking when the endoluminal prosthesis is deployed. Furthermore, the ability of the endoluminal prosthesis to have controlled folding is advantageous because it prevents the lumen of the prosthesis from closing, which could prevent the flow of blood to the vessels.

It is to be understood that the features of the various embodiments taught herein may be combined together to form new embodiments, these being within the scope of the teachings herein and the claims.

BRIEF DESCRIPTION OF THE DRAWINGS

Embodiments of the present invention are described below, by way of example only, with reference to the accompanying drawings, in which.

DESCRIPTION OF THE PREFERRED EMBODIMENTS

Figure 1:
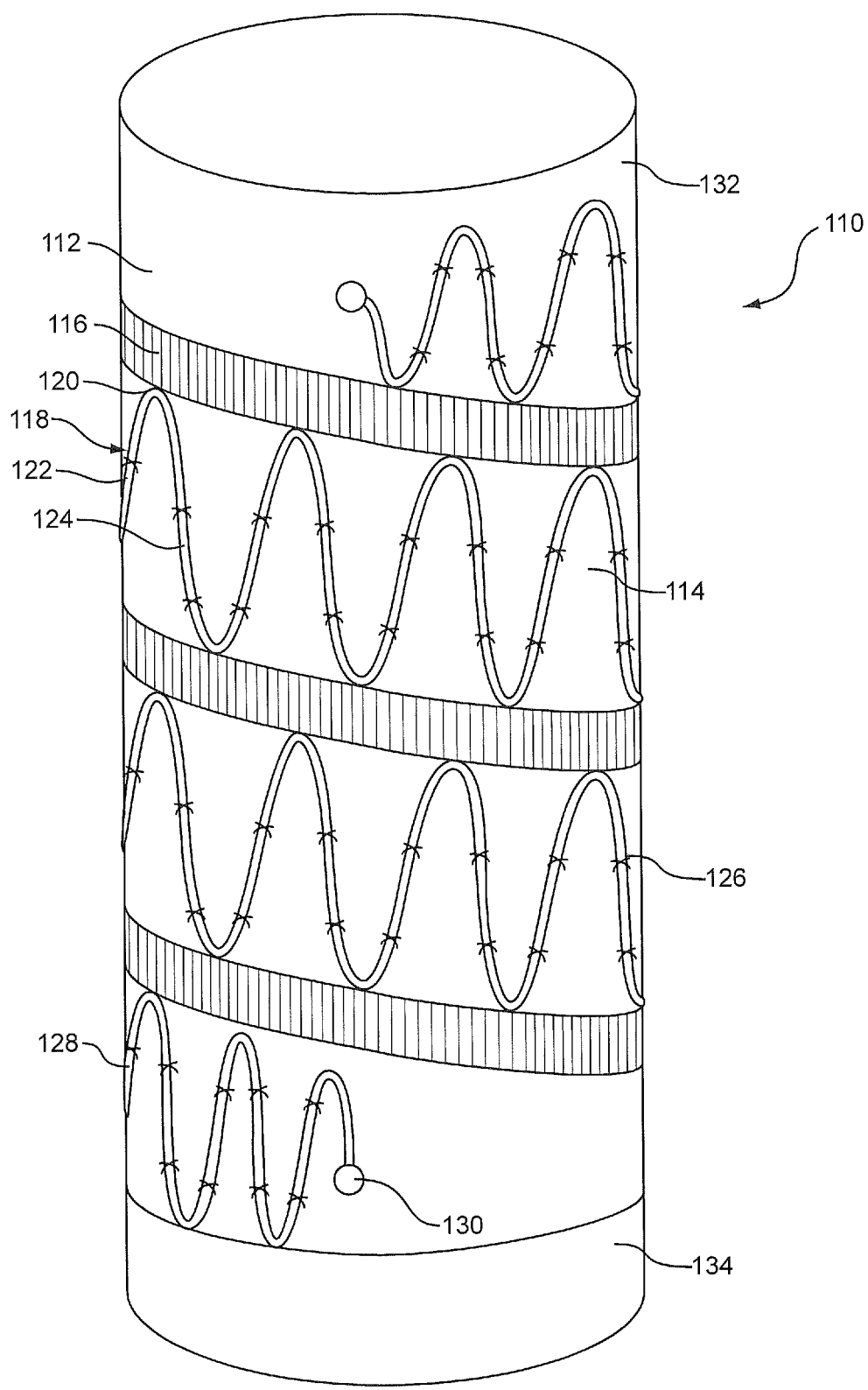
FIG. 1 illustrates an endoluminal prosthesis having a uniform section throughout the length of the endoluminal prosthesis in a first condition.

Unless defined otherwise, all technical and scientific terms used herein have the same meaning as commonly understood to one of ordinary skill in the art to which this invention belongs.

The term "prosthesis" also means any replacement for a body part or function of that body part. It may also mean a device that enhances or adds functionality to a physiological system.

The term "tubular" refers to the general shape of an endoluminal device which allows the module to carry fluid along a distance or fit within a tubular structure such as an artery. Tubular prosthetic devices include single, branched, and bifurcated devices. Tubular may refer to any shape including, but not limited to, tapered, cylindrical, curvilinear, or any combination thereof.

The term "endoluminal" refers to or describes objects that can be placed inside or moved through a lumen or a body passageway in a human or animal body. A lumen or a body passageway can be an existing lumen or a lumen created by surgical intervention. As used in this specification, the terms "lumen" or "body passageway," and "vessel" are intended to have a broad meaning and encompasses any duct (e.g., natural or iatrogenic) or cavity within the human body and can include a member selected from the group comprising: blood vessels, respiratory ducts, gastrointestinal ducts, and the like. Accordingly, the terms "endoluminal device" or "endoluminal prosthesis" describe devices that can be placed inside or moved through any such lumen.

The term "graft" or "graft material" describes an object, device, or structure that is joined to or that is capable of being joined to a body part to enhance, repair, or replace a portion or a function of that body part. A graft by itself or with the addition of other elements, such as structural components, can be an endoluminal prosthesis. The graft comprises a single material, a blend of materials, a weave, a laminate, or a composite of two or more materials. The graft can also comprise polymer material that may be layered onto a mandrel. Preferably, polymers, although added in layers onto the mandrel, after curing, result in one layer that encapsulates an endoluminal prosthesis or woven graft. This also aids in decreasing the incidence of delamination of the resulting endovascular prosthesis. Biological scaffold, such as a bioremodelable material, such as small intestine submucosa, which is commercially available by Cook Biotech, West Lafayette, Ind.

The terms "patient," "subject," and "recipient" as used in this application refer to any mammal, particularly humans.

The term "helical" as used in this specification refer to any shape extending in a direction having both longitudinal and circumferential components, for example, a three dimensional form or shape. Thus the term encompasses circular helixes, general helixes, cylindrical helixes, conic helixes, and the like. The helical shape may twist uniformly about a central axis, or may be asymmetrical. A helix can also be understood to refer to a two dimensional shape, commonly understood to be a spiral.

The term "yarn" refers to a length of a continuous thread or strand of one or more filaments or fibers, with or without twist, suitable for weaving, knitting or otherwise intertwining to form a textile fabric.

The term "longitudinally" refers to a direction, position or length substantially parallel with a longitudinal axis of a reference, and is the length-wise component of the helical orientation.

The term "circumferentially" refers to a direction, position, or length that encircles a longitudinal axis of reference. Circumferential is not restricted to a full 360° circumferential turn nor a constant radius.

The term "biocompatible" refers to a material that is substantially non-toxic in the in vivo environment of its intended use, and that is not substantially rejected by the patient's physiological system (i.e., is non-antigenic).

In the description which follows, it is to be understood that references to the constitution of a graft include the graft being made of the material or including the stated material, that is to be made substantially entirely of the material or to include the material as one of a plurality of components.

Figure 2:
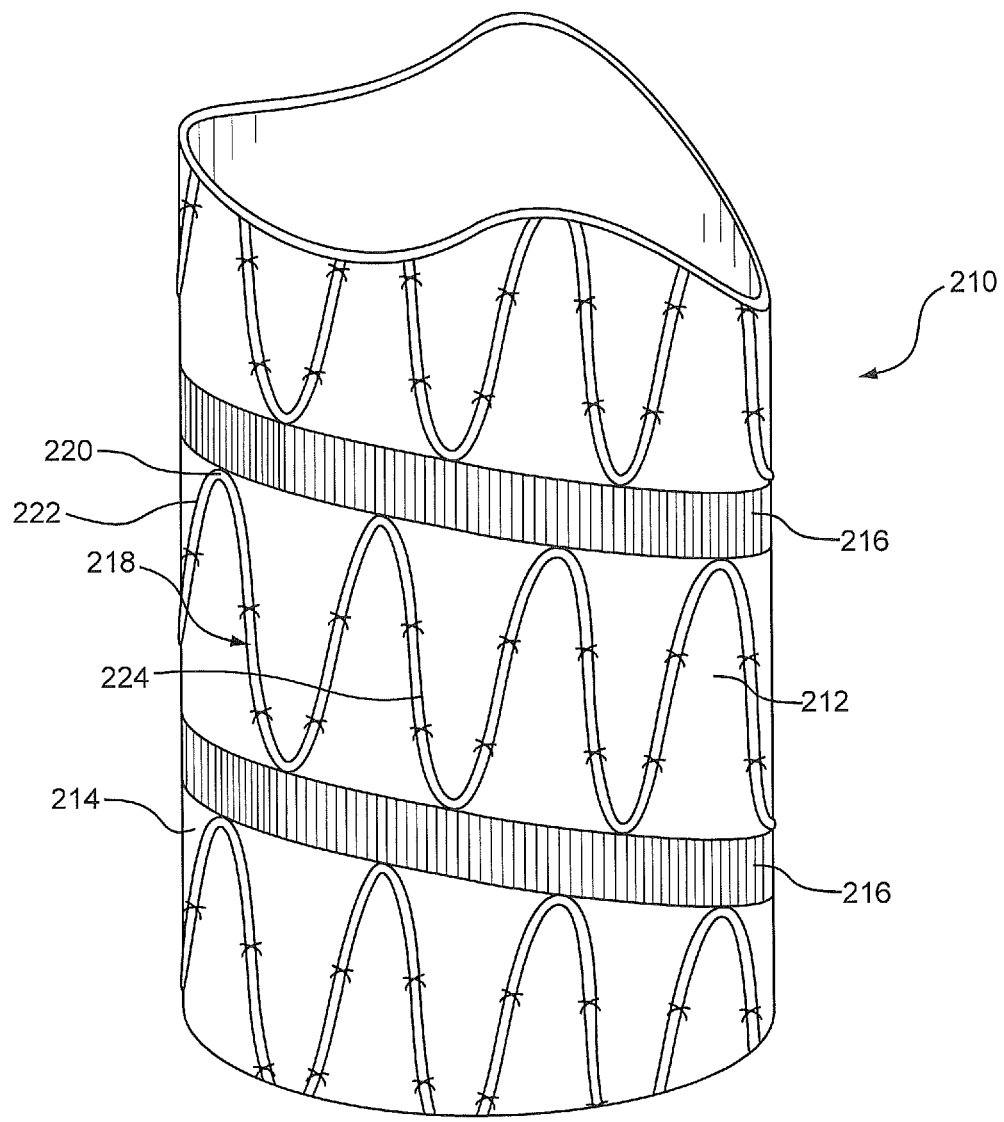
FIG. 2 illustrates a portion of a thin region of the endoluminal prosthesis of FIG. 1.

FIG. 1 provides an embodiment of the endoluminal prosthesis 110. The endoluminal prosthesis 110 comprises a graft 112 configured to be placed within a diseased vessel in a first position, where the first position is substantially straight. The graft 112 may have a generally tubular configuration having a lumen disposed therebetween. As shown in FIGS. 1 and 2, the graft 112 includes first regions 114, 214 comprising a first biocompatible material, and second regions 116, 216 comprising a second biocompatible material. The second regions 116, 216 are spirally positioned upon the graft 112 with respect to the first biocompatible material of the first regions 114, 214. Further, the second regions 116, 216 extend longitudinally throughout the entire length of the graft 112, 212, while also being positioned about the circumference of the graft 112, 212.

Examples of biocompatible materials from which textile graft material can be formed include polyesters, such as poly(ethylene terephthalate); fluorinated polymers, such as polytetrafluoroethylene (PTFE) and fibers of expanded PTFE; and polyurethanes. In addition, materials that are not inherently biocompatible may be subjected to surface modifications in order to render the materials biocompatible. Examples of surface modifications include graft polymerization of biocompatible polymers from the material surface, coating of the surface with a cross linked biocompatible polymer, chemical modification with biocompatible functional groups, and immobilization of a compatibilizing agent such as heparin or other substances. Thus, any fibrous material may be used to form a textile graft, provided the final textile is biocompatible. Textile materials that can be formed into fibers suitable for making textile grafts include polyethylene, polypropylene, polyaramids, polyacrylonitrile, nylons and cellulose, in addition to polyesters, fluorinated polymers, and polyurethanes as listed above. It is also to be understood that bioremodelable materials may be used singly or in combination with the aforementioned polymer materials. Preferably the textile is made of one or more polymers that do not require treatment or modification to be biocompatible. The graft is preferably constructed from a material such as woven multifilament polyester.

One example of biocompatible polyester include Dacron™ (DuPONT, Wilmington, Del.), which is known to be sufficiently biologically inert, non-biodegradable, and durable to permit safe insertion inside the human body. Polyester is also known to excite fibrous in growth which will secure the graft to the wall of the lumen within a few months of its insertion. Any material with such qualities may be used, however. Laser bonding may be utilized to form the graft into a tubular configuration. In some embodiments of the endoluminal prosthesis 110, the first biocompatible material and the second biocompatible material are manufactured from the same material. In other embodiments, the second biocompatible material is manufactured from a material having a greater flexibility than the first biocompatible material.

Referring back to FIG. 2, the endoluminal prosthesis 210 may comprise any kind of weave. For example, the endoluminal prosthesis 210 may include, but is not limited to, weaves such as plain weaves, basket weaves, rep or rib weaves, twill weaves (e.g., straight twill, reverse twill, herringbone twill), satin weaves, and double weaves (e.g., double-width, tubular double weave, reversed double weave). Desirably, the weave comprises a tubular double layer weave. The endoluminal prosthesis 210 may be woven in any suitable manner. For example, the fabric may be woven on a table loom, a floor loom, a jacquard loom, a counterbalance loom, a jack loom, or an upright loom. Desirably, the fabric is woven on a floor loom. The fabric may have any configuration possible, but preferably has warp and weft yarns. In one embodiment, both the warp yarns and the weft yarns are textile yarns. Determination of which combination of materials woven in which direction of the textile graft that is most appropriate may be based on the type of clinical application, properties of the textile graft that are desired, and further factors such as the weave type, yarn properties such as the size or denier of the yarn, finishing techniques, and/or permeability of the textile. For example, for percutaneous application, thin textile grafts are preferred. Such thin grafts comprise yarns that have are fine or have a low denier.

Figure 4:
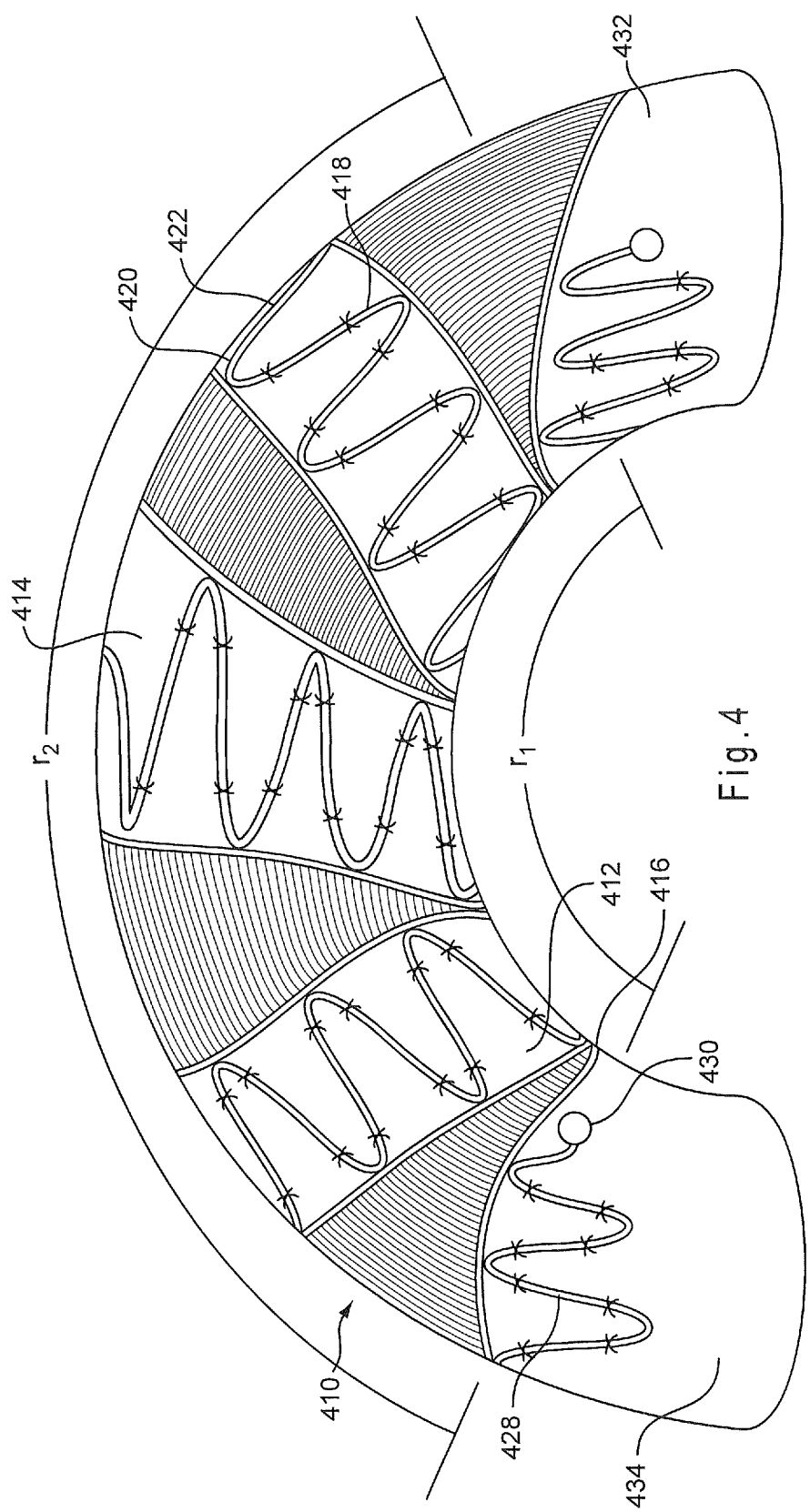
FIG. 4 illustrates the endoluminal prosthesis of FIG. 1 in a second, bent or curved condition.

The second regions 216 of the prosthesis 210 may comprise the same weave or a different weave pattern from the remainder of the graft 212. The second regions 216 may be woven, for example, by dropping and adding yarns, by fast/slow take-up, and by having more than one weave design. Preferably, the second regions 216 of the prosthesis 210 have the same weave as that of the remainder of the graft 212. The second regions 216 in the endoluminal prosthesis provide specific areas for the graft to fold when endoluminal prosthesis is positioned in a tortuous, or curved, position. In particular, the second regions 216 may be narrower than the first regions of the graft 212, which helps to assist the graft 212 to fold in those precise areas when the graft 212 is placed in a curved position. When the endoluminal prosthesis is bent, as shown in FIG. 4, the force applied to endoluminal prosthesis is distributed first to the second regions, which allows for controlled folding through the endoluminal prosthesis as opposed to concentrating on one particular section of the endoluminal prosthesis.

Referring back to FIG. 2, the first biocompatible material may have a weave density that is greater than the weave density of the yarns comprising the second regions 214 of the endoluminal prosthesis 210. The difference in the weave density of the yarn aids in the reduction of kinking in the prosthesis 210 because the less dense yarns of the second regions 214 will fold prior to the remaining portions of the graft upon the application of force. The yarns used in the second regions 216 may have different heat setting characteristics than the yarns used in the rest of the graft 112. In addition, the yarns used in the second regions 216 may also have a greater flexibility than the yarns used in the other sections of the graft 212. Furthermore, the second region 216 may be comprised of yarns having a lower denier than the yarns used in the first region 214, which may also contribute to the difference in the density between the two regions.

During the weaving process to create the graft, the sett and pick count are kept constant. The sett may be between about 50 and about 300 ends per inch and the pick count may be between about 50 and about 300 picks per inch. An "end" refers to an individual warp yarn, and a "pick" refers to an individual weft yarn. In one embodiment, the textile graft comprises a plain weave having 150 ends per inch and 250 picks per inch. In another aspect, the density of the yarns used in the second regions 216 of the prosthesis 210 and the yarns used in the rest of the graft may be altered based on the needs of the patient. For example, one may achieve an increased density in the first biocompatible material in the direction of the warp yarns by weaving the weft yarns at a slower speed and by changing the sett and pick count of the weave. This increased density provides increased structural support in the first biocompatible material, which can benefit a patient suffering from vessels having an advanced diseased state.

After the graft is weaved, the second regions of the graft are formed into the desired configuration. For example, the second regions 216 of the graft material are formed into a helix. As shown in FIG. 2, this helix may be left-handed, although in other embodiments it may be right handed. Prior to heat setting, the graft 212 may be placed over a mandrel having a helical configuration in the desired pattern for the second regions 216 on the endoluminal prosthesis 210. In addition, a wire may be wound about the circumference of the graft 212 along the second regions 216 of the graft in order to keep the helical design in place. Then the graft 212 is subject to the process of heat setting. During the heat setting process, the second regions 216 are set into the helical formation due to the heat setting characteristics of the yarn material and the form of the mandrel. Following this heat setting process, the graft 212 is allowed to cool, and the second regions 216 are in a helical formation.

Referring to FIGS. 1 and 2, the endoluminal prosthesis 110, 210 includes an elongate member 118, 218 attached to the prosthesis 110 longitudinally and circumferentially. The elongate member 118, 218 has a plurality of bends 120, 220, or apices, which connect a pair of first struts 122, 212 and second struts 124, 224 at an angle. Each of the first struts 122, 222 extend from adjacent bends 120, 220 in a first direction. In addition, each of the second struts 124 extends between adjacent bends in a second direction, where the second direction is different than the first. Preferably, each of the first struts 122, 222 have substantially the same length and each of the second struts substantially the same length, the length of the first struts 122, 222 being longer than the length of the second struts 124, 224. In other embodiments, the length of the second struts 124, 224 may be shorter than length of first strut 122, 222. In addition, the angle formed between the first struts 122, 222 and second struts 124, 224 at the bends is generally uniform. Preferably, the angle between first struts 122, 222 and second struts 124, 224 and the bends 120, 220 is between about 20 and about 120 degrees, and more preferably between 45 and 70 degrees. In other embodiments, the elongate member 118 may not include a plurality of first and second struts.

Referring back to FIG. 1, the elongate member 118 may be attached to the endoluminal prosthesis 110 by conventional means, including the use of suture material. In some embodiments, the suture material is only sewn about the bends 120 of the elongate member 114 to the endoluminal prosthesis 110. In other embodiments, the suture material may be sewn about the bends 120, as well as, the first and second struts 122, 124 of the elongate member 118. The elongate member 118 may be formed into other suitable configurations, including, but not limited to, a helical coil. In other embodiments, the elongate member 118 may not include a plurality of first and second struts. As stated above, the elongate member 118 may comprise a substantially mono-planar, flat form. In some embodiments, the elongate member 118 may have a three dimensional form.

Preferred materials include those materials that can provide the desired functional characteristics with respect to mechanical load bearing, biological compatibility, modulus of elasticity, or other desired properties. In various embodiments, the elongate member 118 may include a metallic material selected from stainless steel, silver, platinum, palladium, gold, titanium, tantalum, iridium, tungsten, cobalt, chromium, cobalt-chromium alloy 1058, cobalt-based 35N alloy, nickel-based alloy 625, a molybdenum alloy, a molybdenum alloy including about 0.4% to about 0.8% of lanthanum oxide ($Li_2O_3$), and a nickel-titanium alloy, such as Nitinol, or other suitable materials as known in the art.

The endoluminal prosthesis 110 may include a plurality of turns 126. As stated above, the turns may be positioned upon the outer surface of the graft both longitudinally and circumferentially. The turns 126 in the first section of the endoluminal prosthesis 110 are in alignment about its circumference. In addition, at least one of the bends 120 may be circumferentially aligned with the bends 120 on a longitudinally adjacent turn. This alignment of the bends on the turns 126 of the elongate member contributes to the reduction of kinking upon deployment of the endoluminal prosthesis 110. As discussed further below, an end portion 130 is located on the final turn 128 of the elongate member 118. The endoluminal device 110 also includes a first end 132 and a second end 134. A sealing stent may be placed within the interior surface of the endoluminal prosthesis 110 at the ends. The sealing stents may be attached to the first end 132 and the second end 134 of the endoluminal prosthesis 110 by conventional attaching mechanism, including the use of suturing.

Each turn of the elongate member 118 has a predetermined number of bends extending 360 degrees around a central axis. The second regions located between each turn may have a width from about 0 to about 8 millimeters. In some embodiments, the second regions 116 have a spacing between the longitudinally adjacent turns of the elongate member 118 of about 4 mm. In addition, the predetermined number of bends 120 on each turn may range from 2 and 9 bends depending on a number of different construction variables. Preferably, the number of bends 120 in each turn is between 4 and 6 bends, and more preferably the number of bends 120 in each helical turn of the elongate member 118 is five. Thus, the spacing between each longitudinally adjacent turn is kept generally constant.

Figure 3:
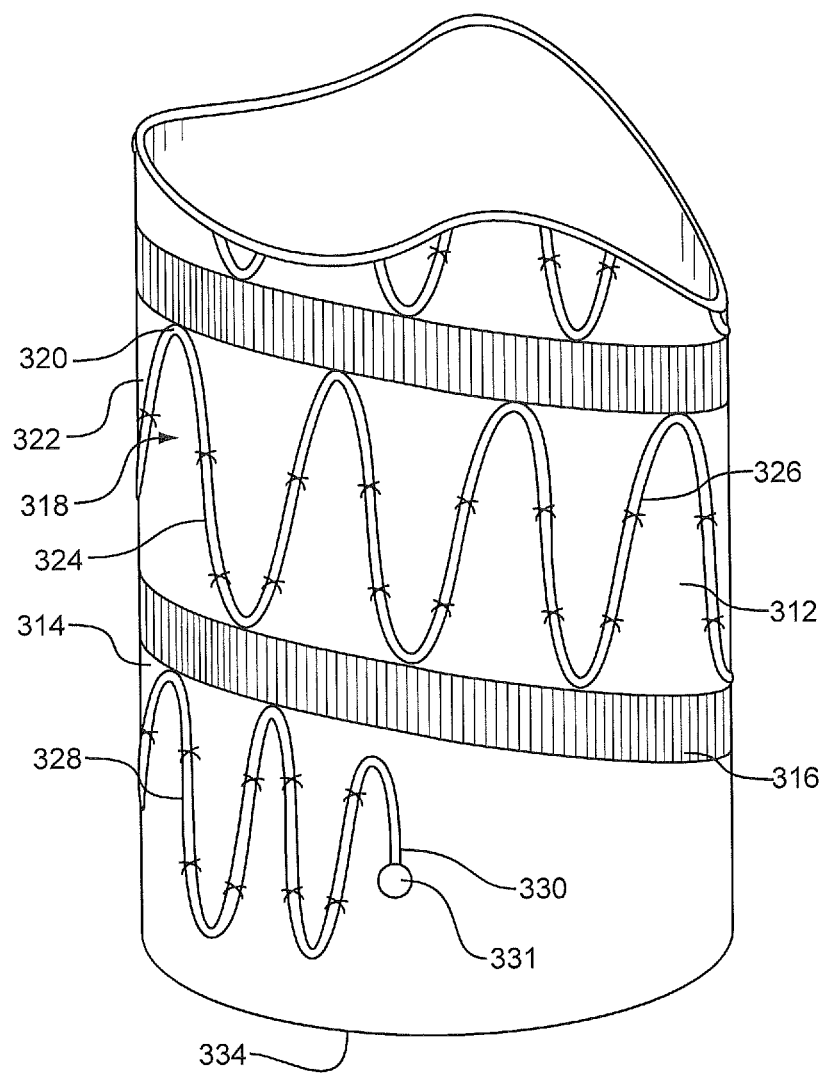
FIG. 3 illustrates an end portion of the endoluminal prosthesis of FIG. 1.

Referring to FIG. 3, an end portion 330 of the elongate member 318 is shown. The elongate member 318 having turns 326, 328 is positioned on the graft 312, which has first regions 314 and second regions 316. The end portion 330 is located on the final turn 328 of the elongate member 318. The final turn 328 of the elongate member 318 consists of a plurality of bends 320 connecting a pair of first 322 and second struts 324, where the angle formed by the converging struts is substantially the same. In addition, the end turn 328 is also in a level configuration with the longitudinally adjacent turn 326. This configuration is important in order to support the remaining portion of the endoluminal device 310. In this embodiment, the end portion 330 of the elongate member 318 is in a generally hook shaped configuration. In other embodiments, the end portion 330 of the member may have other suitable configurations. The end portion 330 of the elongate member 318 includes a terminating end 331. The terminating end 331 in this embodiment comprises a ball. In other embodiments, the elongate member 318 may be terminated by other suitable methods. It is important to choose a terminating end 331 that will be non-traumatic to the both the first compatible material 312 of the graft, as well as, the vessel of the recipient of the prosthesis 310. The end turn 328 is separated from the second end 334 of the endoluminal device by a predetermined distance. This distance may range from about 1 mm to about 3 mm. In some embodiments, the distance between the end turn 328 and the second end 334 is about 1 mm.

FIG. 4 shows an embodiment of the endoluminal prosthesis 410 in a second configuration. As shown, the endoluminal prosthesis 410 comprises a graft 412 having a first end 432 and a second end 434 and is bent such that an interior radius and an exterior radius are present, where the interior radius $r_1$ is smaller than the exterior radius $r_2$ of the graft 412. As the endoluminal prosthesis 410 is placed into the second configuration, the second regions 416 along the interior radius $r_1$ begin to compress. This compression allows for uniform folding about the length of the endoluminal device 410. This feature is important so that the compression force is not concentrated in one area of the endoluminal device 410, which may cause a more significant amount of folding or kinking. This kinking may close the lumen of the graft and the graft may have to be repositioned by a later procedure. The uniform folding of the second regions 416 along the interior radius $r_1$ allows the lumen to remain substantially open. This improvement is significant as it reduces possibility of kinking when the endoluminal prosthesis is deployed. The elongate member 418 is positioned on the first region 414 of the graft and has a plurality of bends 420, or apices, which connect a pair of first 422 and second struts 424 at an angle. An end portion 430 is located on the final turn 428 of the elongate member 418 of the graft 412.

Figure 5:
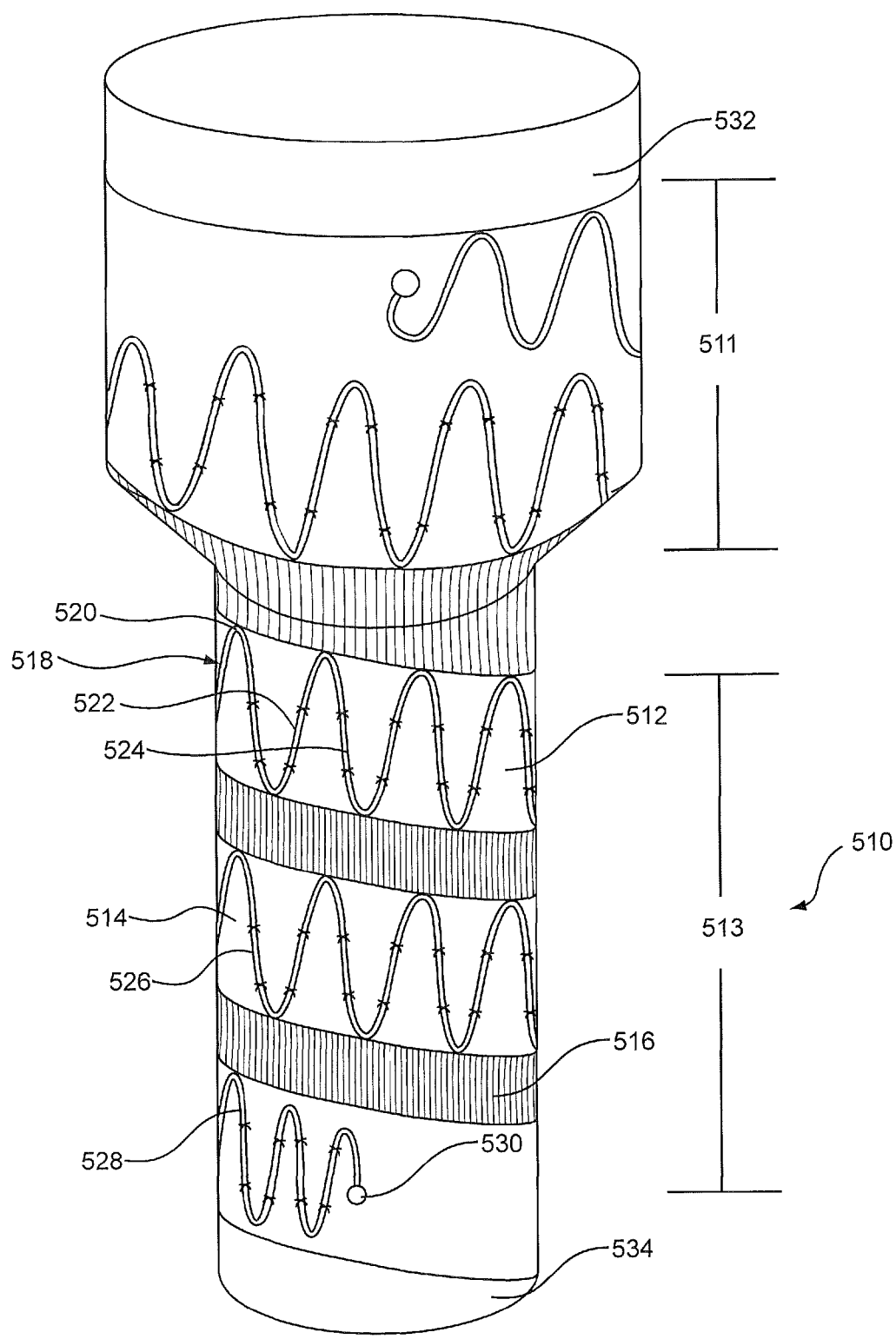
FIG. 5 illustrates an endoluminal prosthesis having a uniform section and a tapered section in a first condition.

Referring to FIG. 5, the endoluminal prosthesis 510 illustrates another embodiment of a graft 512 having a tapered section 511 having a diameter that increases throughout the length of the section. The endoluminal prosthesis 510 also includes a uniform section 513 with a generally constant diameter throughout the length of the section. In some embodiments, the uniform section 513 has a uniform diameter of about 13 mm and a length of about 56 mm. The tapered section 511 may have a diameter that ranges from about 13 mm to about 24 mm. As shown by FIG. 5, the second section forms a taper throughout the length of the section. This tapered section 511 is designed to accommodate the size of the vessel. The tapered section 511 may be either symmetrical or asymmetrical. The length of the uniform section 513 may be about 17 mm. The endoluminal prosthesis 510 is comprised of first regions 514 comprising a first biocompatible material and second, thinner regions 516 comprising a second biocompatible spirally positioned about a central axis with respect to the first regions 514 of the graft. As stated above, second regions 516 of the present embodiment have a lighter denier than the first biocompatible material and are formed into the graft in a left-hand helix. The graft 512 also includes a first end 532 and a second end 534.

As shown in FIG. 5, an elongate member 518 is attached to the outer surface of the graft. The elongate member 518 is attached to the graft longitudinally and circumferentially. The elongate member 518 includes a plurality of turns 526 throughout both the uniform section of the graft and the tapered section of the graft. The elongate member 518 has a plurality of bends 520, which connect a pair of first 522 and second struts 524 at an angle. Each of the first struts 522 extend from adjacent bends 520 in a first direction. In addition, each of the second struts 524 extends between adjacent bends 520 in a second direction, where the second direction is different than the first. An end portion 530 is located is located on the final turn 528 of the elongate member 518.

The uniform section 513 and the tapered section 511 of the graft include turns 526 that are positioned upon the outer surface of the endoluminal prosthesis 510 both longitudinally and circumferentially. The turns 526 are in alignment about the circumference. Throughout the tapered section 511 of the endoluminal prosthesis 510, the first struts 522 are shorter in lengths than the second struts 524. The angle between the converging struts gets progressively larger as the diameter of the tapered section 511 increases. This occurs in each turn of the elongate member 518 in the second section. In one embodiment, the ratio between the length of the first and second struts 522, 524 in the tapered section of the graft is substantially the same for each pair of first and second struts 522, 524. In another embodiment, the lengths of each successive first and second struts 522, 524 in the tapered section 511 of the endoluminal prosthesis 510 may be increased by a progressively smaller amount moving in the direction from a first end toward a second end. In still another embodiment the ratio between the length of the first and second struts 522, 524 in the tapered section 511 of the endoluminal prosthesis 510 increases moving from a first end toward a second end for each pair of first and second struts 522, 524.

Figure 6:
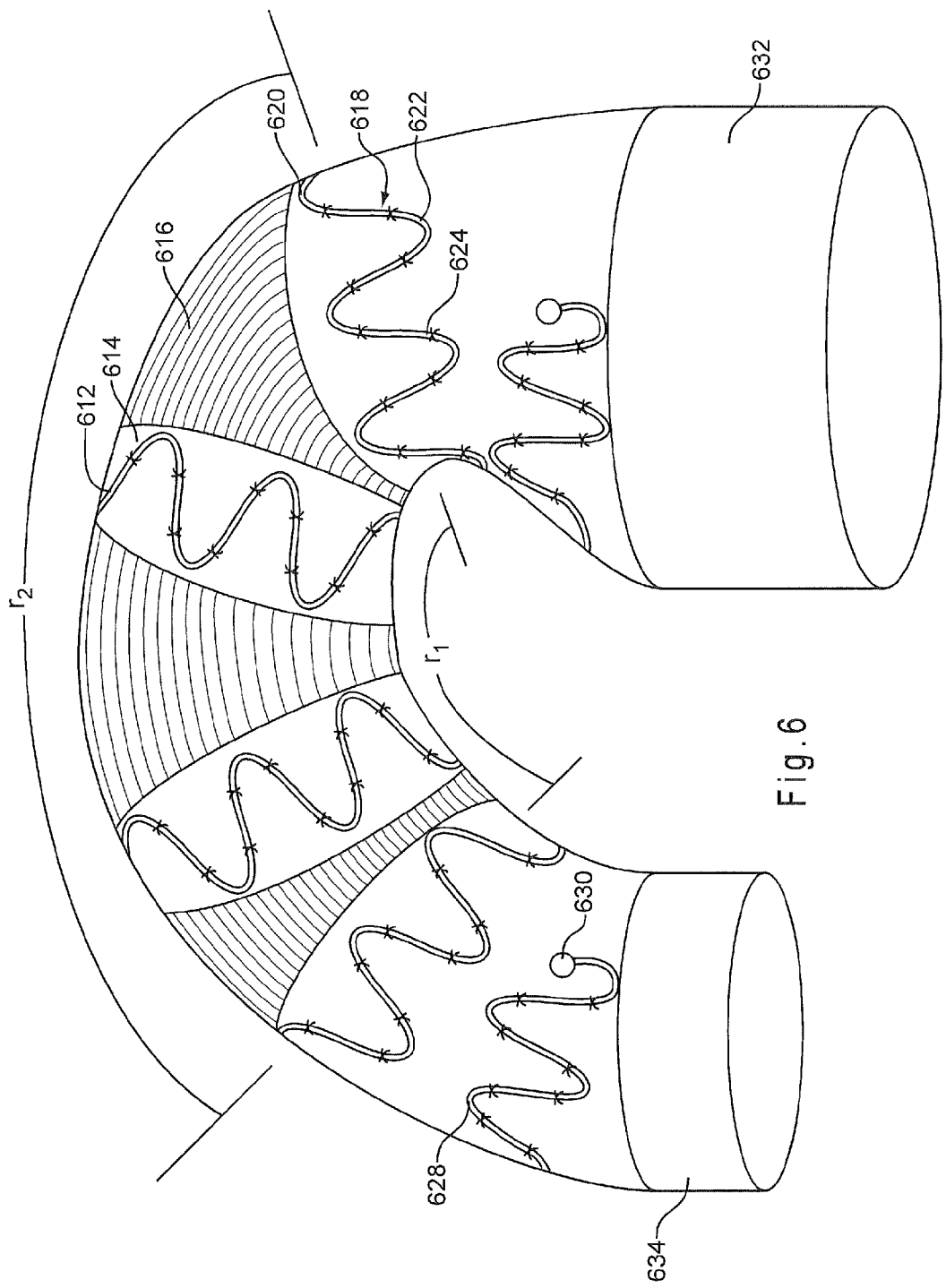
FIG. 6 illustrates the endoluminal prosthesis of FIG. 5 in a second, bent or curved condition.

FIG. 6 show an embodiment in a second configuration. The endoluminal prosthesis 610 is bent such that an interior radius and an exterior radius of the graft 612 are present, where the interior radius $r_1$ is smaller than the exterior radius $r_2$ of the graft. As shown, the endoluminal prosthesis 610 comprises a graft 612 having a first end 632 and a second end 634 and is bent such that an interior radius and an exterior radius are present, where the interior radius $r_1$ is smaller than the exterior radius $r_2$ of the graft 612. As the endoluminal prosthesis 610 is placed into the second configuration, the second regions 616 along the interior radius $r_1$ begin to fold or curve, which distributes the compression forces through the entire device rather than in one concentrated location. The uniform folding of the second regions 616 along the interior radius $r_1$ allows the lumen to remain substantially open. The elongate member 618 is positioned on the first region 614 of the graft and has a plurality of bends 620, or apices, which connect a pair of first 622 and second struts 624 at an angle. An end portion 630 is located on the final turn 628 of the elongate member 618 of the graft 612.

Figure 7:
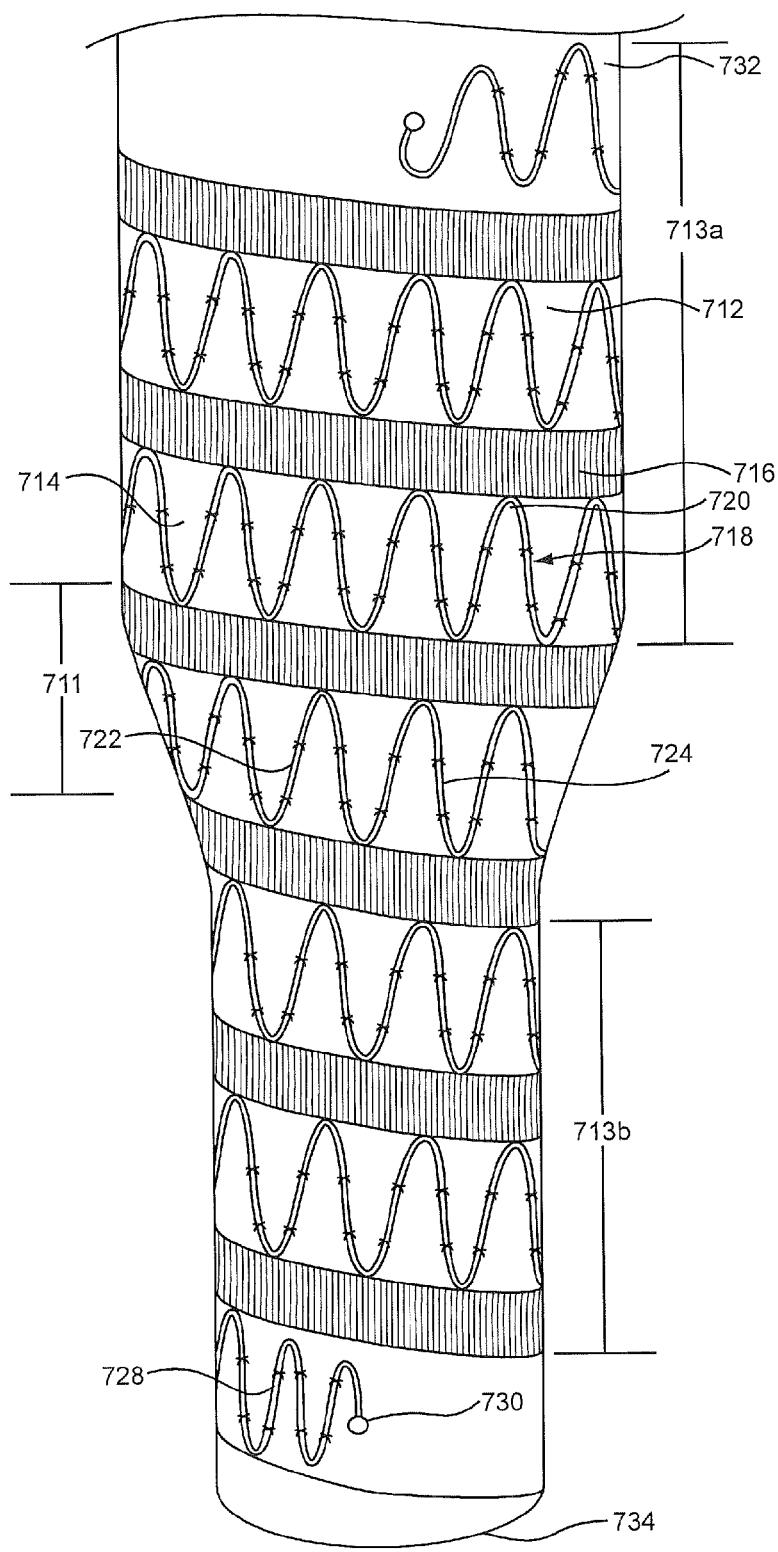
FIG. 7 illustrates an endoluminal prosthesis having two uniform sections and one tapered section in a first condition.

FIG. 7 depicts another embodiment of the endoluminal prosthesis. The endoluminal prosthesis 710 comprises a graft 712 having a first end 732 and a second end 734. The endoluminal prosthesis 710 has two uniform sections with a generally uniform diameter 713a, 713b, and a tapered section 711 where the diameter varies throughout the length of the section 713. In some embodiments, the first uniform section 713a has a diameter of about 11 mm and a length from about 34 to about 51 mm. In some embodiments, the second uniform section 713b has a diameter of about 9 mm and a length of from about 34 to about 51 mm. The tapered section 711 may have a diameter that ranges from about 9 mm at one end to about 13 mm at another end. This tapered section 711 is pivotal in order to accommodate the size of the vessel. The length of the tapered section may be about 3 to about 34 mm. The endoluminal prosthesis 710 also includes a first end 732 and a second end 734. A sealing stent may be placed within the interior surface of the endoluminal prosthesis 710 at the ends. The sealing stents may be attached to the first end 732 and the second end 734 of the endoluminal prosthesis 710 by conventional attaching mechanism, including the use of suturing.

As shown, the endoluminal prosthesis 710 is in a first condition, where the endoluminal prosthesis is substantially straight. The endoluminal prosthesis may also have a second, curved condition having an interior radius and an exterior radius. The elongate member 718, having a plurality of bends 720 connecting a pair of first 722 and second struts 724 at an angle, is attached to the graft 712 longitudinally and circumferentially and has the configuration of a left-hand helix. A plurality of turns is positioned upon the outer surface of the graft both longitudinally and circumferentially in circumferential alignment on the graft. An end portion 730 is located on the final turn 728 of the elongate member 718 of the graft 712.

The endoluminal prosthesis 710 is comprised of first regions 714 comprising a first biocompatible material and second, thinner regions 716 comprising a second biocompatible material spirally positioned about a central axis with respect to the first regions 714 of the graft. As stated above, second regions 716 of the present embodiment have a lighter denier than the first biocompatible material and are formed into the graft in a left-hand helix. Preferably, the second regions 716 of the prosthesis 710 have the same weave as that of the remainder of the graft 712.

While preferred embodiments of the invention have been described, it should be understood that the invention is not so limited, and modifications may be made without departing from the invention. The scope of the invention is defined by the appended claims, and all devices that come within the meaning of the claims, either literally or by equivalence, are intended to be embraced therein. Furthermore, the advantages described above are not necessarily the only advantages of the invention, and it is not necessarily expected that all of the described advantages will be achieved with every embodiment of the invention.

The invention claimed is:

1. An endoluminal prosthesis, comprising:
   a tubular graft comprising a woven first biocompatible material having a first weave density comprising yarns aligned in a first direction interwoven with yarns aligned in a second direction, and a woven second biocompatible material having a second weave density less than the first weave density comprising yarns aligned in a first direction interwoven with yarns aligned in a second direction, the woven second biocompatible material being spirally positioned throughout substantially the entire length of the tubular graft around a central axis with respect to the first biocompatible material; and an elongate member sutured along the length of the tubular graft, the elongate member having a plurality of bends, each bend connecting a pair of first struts and second struts at a first angle, each of the first struts having a length and the second struts having a length, where the length of the first struts is longer than the second struts;

wherein the tubular graft includes first regions made from the woven first biocompatible material and second regions made from the woven second biocompatible material, the yarns aligned in the first direction and the second direction of the woven second biocompatible material in the second regions having different heat setting characteristics than the yarns aligned in the first direction and the second direction of the woven first biocompatible material in the first regions, and wherein the elongate member is sutured to the first regions of the tubular graft.

2. The endoluminal prosthesis of claim 1, wherein the woven second biocompatible material is disposed on the tubular graft in a helix.

3. The endoluminal prosthesis of claim 2, wherein the woven second biocompatible material is disposed on the tubular graft in a left-hand helix.

4. The endoluminal prosthesis of claim 1, wherein the woven first biocompatible material and the woven second biocompatible material are comprised of the same material.

5. The endoluminal prosthesis claim 1, wherein the woven second biocompatible material has a width from greater than 0 millimeters to about 8 millimeters.

6. The endoluminal prosthesis of claim 1, wherein the woven second biocompatible material has a width of about 4 millimeters.

7. The endoluminal prosthesis of claim 1, wherein the elongate member is sutured under torsion to the tubular graft.

8. The endoluminal prosthesis of claim 1, wherein the elongate member is longitudinally and circumferentially sutured to the tubular graft.

9. The endoluminal prosthesis of claim 1, wherein the woven first biocompatible material comprises yarns having a first denier, and the woven second biocompatible material comprises yarns having a second denier less than the first denier.

10. The endoluminal prosthesis of claim 1, wherein the second regions are narrower than the first regions.

11. An endoluminal prosthesis, comprising:

a tubular graft comprising a woven first biocompatible material having a first flexibility and a woven second biocompatible material having a second flexibility greater than the first flexibility, the second biocompatible material spirally positioned throughout substantially the entire length of the tubular graft around a central axis with respect to the first biocompatible material; and an elongate member sutured along the length of the tubular graft, the elongate member having a plurality of bends, each bend connecting a pair of first struts and second struts at a first angle, each of the first struts having a length and the second struts having a length, where the length of the first struts is longer than the second struts;

wherein the tubular graft includes first regions made from the woven first biocompatible material and second regions made from the woven second biocompatible material, the yarns in the second regions having different heat setting characteristics than the yarns in the first regions, and wherein the elongate member is sutured to the first regions of the tubular graft.

12. The endoluminal prosthesis of claim 11, wherein the woven second biocompatible material is disposed on the tubular graft in a helix.

13. The endoluminal prosthesis of claim 12, wherein the woven second biocompatible material is disposed on the tubular graft in a left-hand helix.

14. The endoluminal prosthesis of claim 11, wherein the woven first biocompatible material and the woven second biocompatible material are comprised of the same material.

15. The endoluminal prosthesis of claim 14, wherein the woven first biocompatible material and the woven second biocompatible material are formed of or include polyester.

16. The endoluminal prosthesis of claim 11, wherein the woven first biocompatible material comprises yarns aligned in a first direction interwoven with yarns a second direction having a first weave density, and the woven second biocompatible material comprises yarns aligned in a first direction interwoven with yarns aligned in a second direction having a second weave density less than the first weave density.

17. The endoluminal prosthesis of claim 11, wherein the woven second biocompatible material has a width of about 4 millimeters.

18. The endoluminal prosthesis of claim 11, wherein the elongate member is sutured under torsion to the tubular graft.

19. The endoluminal prosthesis of claim 11, wherein the elongate member is longitudinally and circumferentially sutured to the tubular graft.

20. An endoluminal prosthesis, comprising:

a tubular graft comprising a woven first biocompatible material having a first weave density comprising yarns aligned in a first direction interwoven with yarns aligned in a second direction, and a woven second biocompatible material having a second weave density less than the first weave density comprising yarns aligned in a first direction interwoven with yarns aligned in a second direction, the second biocompatible material disposed in a helix on the graft;

an elongate member having a plurality of turns sutured longitudinally and circumferentially to the graft, the elongate member comprising a plurality of bends, each bend connecting a pair of first and second struts at a first angle, each of the first struts extending between adjacent bends in a first direction and each of the second struts extending between adjacent bends in a second direction, the second direction being different than the first direction, each of the first struts having a length and the second struts having a length, where the length of the first struts is longer than the second struts;

wherein the tubular graft includes first regions made from the woven first biocompatible material and second regions made from the woven second biocompatible material, the yarns aligned in the first direction and the second direction of the woven second biocompatible material in the second regions having different heat setting characteristics than the yarns aligned in the first direction and the second direction of the woven first biocompatible material in the first regions, wherein the elongate member is sutured to the first regions of the tubular graft, and wherein the second regions are thinner than the first regions.

\* \* \* \* \*